(12) United States Patent
Kubota et al.

(10) Patent No.: US 6,943,264 B2
(45) Date of Patent: Sep. 13, 2005

(54) PREPARATION OF BRANCHED SILOXANE

(75) Inventors: Yasufumi Kubota, Niigata-ken (JP);
Tohru Kubota, Niigata-ken (JP)

(73) Assignee: Shin-Etsu Chemical, Co., Ltd., Tokyo (JP)

( * ) Notice: Subject to any disclaimer, the term of this patent is extended or adjusted under 35 U.S.C. 154(b) by 0 days.

(21) Appl. No.: 10/926,081

(22) Filed: Aug. 26, 2004

(65) Prior Publication Data

US 2005/0049427 A1 Mar. 3, 2005

(30) Foreign Application Priority Data

Aug. 28, 2003 (JP) ........................................ 2003-303849

(51) Int. Cl.$^7$ ................................................. C07F 7/04
(52) U.S. Cl. ........................ 556/440; 556/453; 556/455; 556/456
(58) Field of Search ................................ 556/440, 453, 556/455, 456

(56) References Cited

FOREIGN PATENT DOCUMENTS

| EP | 1213006 A1 | 6/2002 |
|---|---|---|
| JP | 11-217389 A | 8/1999 |
| JP | 2002-68930 A | 3/2002 |
| JP | 3571521 B2 | 7/2004 |
| WO | WO-01/15658 A1 | 3/2001 |

OTHER PUBLICATIONS

Ohkawa, XP002309579, Database CA, Chemical Abstracts Service, Columbus, Ohio, "Preparation of Silicones Having a Siloxy–Group", database accession No. 131:144711 (Aug. 1999).
Voronkov et al.; "Cleavage of the SiOSi grouping by Tetrachlorosilane and Organylchlorosilanes," Doklady Akademii Nauk SSSR, vol. 227, No. 2, pp. 362–365 (1976).
Hasegawa et al.; "Treatment of alkyltriethoxysilanes with Amberlyst 15 cation–exchange resin in the presence of hexamethyldisiloxane," Journal of Organometallic Chemistry, vol. 340 pp. 31–36 (1988).

*Primary Examiner*—Samuel Barts
(74) *Attorney, Agent, or Firm*—Birch, Stewart, Kolasch & Birch, LLP

(57) ABSTRACT

By reacting a branched siloxane compound of formula (2) containing compounds of formula (1) as an impurity with a disiloxane compound of formula (3) in the presence of an acid compound, there is prepared a branched siloxane of formula (2) containing a reduced level of compounds of formula (1).

$$R^1{}_n Si(OSiR^2{}_3)_{3-n}(OR^3) \qquad (1)$$

$$R^1{}_n Si(OSiR^2{}_3)_{4-n} \qquad (2)$$

$$R^2{}_3 SiOSiR^2{}_3 \qquad (3)$$

$R^1$ is a monovalent hydrocarbon group, $R^2$ and $R^3$ are H or monovalent hydrocarbon groups, and n is 0 or 1.

6 Claims, 4 Drawing Sheets

PREPARATION OF BRANCHED SILOXANE

CROSS-REFERENCE TO RELATED APPLICATION

This Nonprovisional application claims priority under 35 U.S.C. §119(a) on Patent Application No. 2003-303849 filed in Japan on Aug. 28, 2003, the entire contents of which are hereby incorporated by reference.

TECHNICAL FIELD

This invention relates to a method for preparing branched siloxanes, including low-molecular weight branched siloxanes useful as siloxane industrial oils, cosmetic oils, detergents and the like, such as methyltris(trimethylsiloxy)silane and tetrakis(trimethylsiloxy)silane, as well as branched siloxanes useful as reactants for electronic materials, monomers for contact lenses and the like, such as 3-acryloxypropyltris(trimethylsiloxy)silane, 3-methacryloxypropyltris(trimethylsiloxy)silane, p-styryltris(trimethylsiloxy)silane, 5-norbornenyltris(trimethylsiloxy)silane, 2-(5-norbornenyl)ethyltris(trimethylsiloxy)silane, and 2-(5-norbornenyl)ethyltris(dimethylvinylsiloxy)silane.

BACKGROUND ART

Low-molecular weight branched siloxanes include branched tetrasiloxanes such as methyltris(trimethylsiloxy)silane, 3-acryloxypropyltris(trimethylsiloxy)silane and 3-methacryloxypropyltris(trimethylsiloxy)silane, and branched pentasiloxanes such as tetrakis(trimethylsiloxy)silane. They are used as industrial oils, cosmetic oils, detergents, reactants for electronic materials, monomers for contact lenses and the like. Besides, 5-norbornenyltris(trimethylsiloxy)silane, 2-(5-norbornenyl)ethyltris(trimethylsiloxy)silane, and 2-(5-norbornenyl)ethyltris(dimethylvinylsiloxy)silane are important as monomers for ring-opening metathesis polymerization. In particular, 2-(5-norbornenyl)ethyltris(dimethylvinylsiloxy)silane is also useful as a crosslinker and a reactant for the synthesis of dendrimers. Of these applications, the use as cosmetic oils requires a high purity. It is desired to suppress the level of impurity components of one silicon atom to 0.1 wt % or below because they can be irritative to the skin, and to minimize the amount of linear and cyclic compounds of two or three silicon atoms because they can also be irritative to the skin. Similarly a high purity is desired for 3-acryloxypropyltris(trimethylsiloxy)silane, 3-methacryloxypropyltris(trimethylsiloxy)silane and p-styryltris(trimethylsiloxy)silane since they are used as monomers for contact lenses.

It is desired that methyltris(trimethylsiloxy)silane for use as cosmetic oils and 3-acryloxypropyltris(trimethylsiloxy)silane, 3-methacryloxypropyltris(trimethylsiloxy)silane and p-styryltris(trimethylsiloxy)silane for use as contact lens-forming monomers contain reduced levels of low-boiling silicon-containing components and be of high purity.

Many methods are known for the preparation of branched siloxanes. Known methods for preparing methyltris(trimethylsiloxy)silane, for example, include the following.
(1) Co-hydrolysis of methyltrichlorosilane and trimethylchlorosilane in the presence of methanol is described, for example, in WO 2001/15658 and JP-A 2002-68930.
(2) Reaction of methyltrichlorosilane with hexamethyldisiloxane in the presence of perchloric acid catalyst is described, for example, in Dokl. Akad. Nauk, SSSR, 1976, 227, 362–365.
(3) Reaction of methyltriethoxysilane with hexamethyldisiloxane in the presence of an acidic ion-exchange resin is described, for example, in J. Organomet. Chem., 1988, 340, 31–36.
(4) Reaction of methyltrialkoxysilane with hexamethyldisiloxane in the presence of a carboxylic acid and an acid catalyst is described, for example, in JP-A 11-217389.
(5) A method of adding conc. sulfuric acid to methyltrimethoxysilane, hexamethyldisiloxane and methanol and then adding dropwise a mixture of water and methanol thereto is described, for example, in WO 2001/15658 and JP-A 2002-68930.

These methods, however, have problems. Method (1) needs a large volume of water and results in very low yields due to low selectivity of reaction. Method (2) is unsuitable as an industrial process because perchloric acid which is difficult to handle must be used as the catalyst. Method (3) must use hexamethyldisiloxane in large excess in order to promote conversion, but a large amount of a reaction intermediate, 1,1,1,3,5,5,5-heptamethyl-3-ethoxytrisiloxane is left behind. Thus method (3) is not suitable for producing methyltris(trimethylsiloxy)silane with a high purity. In method (4), a by-product having a similar boiling point, 1,1,1,3,5,5,5-heptamethyl-3-methoxytrisiloxane is produced along with the end compound, methyltris(trimethylsiloxy)silane. The yield is 82% at the stage of reaction solution. However, after the reaction solution is distilled for purification to isolate methyltris(trimethylsiloxy)silane with a high purity, the yield as isolated is estimated to be significantly lower. Method (5) produces methyltris(trimethylsiloxy)silane with a high purity, but in a yield of 70%, which is unsatisfactory. The products of methods (3) to (5), which contain monomethoxysilanes and monohydroxysilanes such as 1,1,1,3,5,5,5-heptamethyl-3-methoxytrisiloxane and 1,1,1,3,5,5,5-heptamethyl-3-hydroxytrisiloxane as impurities, must be distilled or otherwise processed to remove the impurities before methyltris(trimethylsiloxy)silane can be obtained in high purity.

A method of converting methyltris(trimethylsiloxy)silane containing monomethoxysilanes and monohydroxysilanes such as 1,1,1,3,5,5,5-heptamethyl-3-methoxytrisiloxane and 1,1,1,3,5,5,5-heptamethyl-3-hydroxytrisiloxane as impurities to a high purity form by way of reaction to reduce the content of monomethoxysilanes and monohydroxysilanes is unknown in the art.

SUMMARY OF THE INVENTION

As discussed above, it is unknown how to prepare branched siloxanes in high yields, especially how to prepare branched siloxane compounds having a sufficiently high purity to use as cosmetic oils, contact lens-forming monomers, electronic material-forming reactants and the like, including methyltris(trimethylsiloxy)silane, tetrakis(trimethylsiloxy)silane, 3-acryloxypropyltris(trimethylsiloxy)silane, 3-methacryloxypropyltris(trimethylsiloxy)silane, p-styryltris(trimethylsiloxy)silane, 2-(5-norbornenyl)ethyltris(trimethylsiloxy)silane, and 2-(5-norbornenyl)ethyltris(dimethylvinylsiloxy)silane, in high yields while reducing the content of monoorganoxysilane compounds and monohydroxysilane compounds contained therein.

Therefore, an object of the present invention is to provide a method for preparing branched siloxanes of high purity in high yields while reducing the content of monoorganoxysilanes and monohydroxysilanes.

The inventor has discovered that by reacting a branched siloxane compound containing a monoorganoxysilane compound or a monohydroxysilane compound or both as an impurity with a disiloxane compound in the presence of an acid compound, the monoorganoxysilane and monohydroxysilane compounds are converted into branched siloxane compounds whereby the content of monoorganoxysilane and monohydroxysilane compounds is reduced. As a result, a branched siloxane of high purity is obtained.

According to the present invention, there is provided a method for preparing a branched siloxane of the general formula (2), comprising the step of reacting a branched siloxane compound of the general formula (2) containing a compound of the general formula (1) as an impurity with a disiloxane compound of the general formula (3) in the presence of an acid compound, for forming a branched siloxane of formula (2) containing a reduced level of the compound of formula (1). The formulae are:

$$R^1_n Si(OSiR^2_3)_{3-n}(OR^3) \tag{1}$$

$$R^1_n Si(OSiR^2_3)_{4-n} \tag{2}$$

$$R^2_3 SiOSiR^2_3 \tag{3}$$

wherein $R^1$ is a substituted or unsubstituted monovalent hydrocarbon group of 1 to 20 carbon atoms, $R^2$ and $R^3$ are selected from hydrogen and substituted or unsubstituted monovalent hydrocarbon groups of 1 to 20 carbon atoms, $R^2$ may be the same or different, and n is equal to 0 or 1.

Preferably, the acid compound is used in at least an equimolar amount relative to the total of the compound of formula (1). The preferred acid compound is sulfuric acid.

In a preferred embodiment, the branched siloxane compound of formula (2) containing the compound of formula (1) as an impurity has been synthesized by reacting a disiloxane compound of formula (3) with an organoxysilane compound of the general formula (4) in the presence of an acid catalyst.

$$R^1_n Si(OR^4)_{4-n} \tag{4}$$

Herein $R^1$ is as defined above, $R^4$ is a substituted or unsubstituted monovalent hydrocarbon group of 1 to 20 carbon atoms, and n is equal to 0 or 1. More preferably, the branched siloxane compound of formula (2) containing the compound of formula (1) as an impurity has been synthesized by adding the organoxysilane compound of formula (4) to a liquid mixture of the disiloxane compound of formula (3), an alcohol and the acid catalyst for reaction, and further adding water for effecting co-hydrolysis.

The branched siloxane compound of formula (2) is typically selected from the group consisting of methyltris(trimethylsiloxy)silane, tetrakis(trimethylsiloxy)silane, 3-acryloxypropyltris(trimethylsiloxy)silane, 3-methacryloxypropyltris(trimethylsiloxy)silane, p-styryltris(trimethylsiloxy)silane, 5-norbornenyltris(trimethylsiloxy)silane, 2-(5-norbornenyl)ethyltris(trimethylsiloxy)silane, and 2-(5-norbornenyl)ethyltris(dimethylvinylsiloxy)silane.

The method of preparing branched siloxanes according to the invention is successful in preparing branched siloxane compounds having a sufficiently high purity to use as cosmetic oils, contact lens-forming monomers, electronic material-forming reactants and the like, including methyltris(trimethylsiloxy)silane, tetrakis(trimethylsiloxy)silane, 3-acryloxypropyltris(trimethylsiloxy)silane, 3-methacryloxypropyltris(trimethylsiloxy)silane, p-styryltris(trimethylsiloxy)silane, 2-(5-norbornenyl)ethyltris(trimethylsiloxy)silane, and 2-(5-norbornenyl)ethyltris(dimethylvinylsiloxy)silane, in high yields while reducing the content of monoorganoxysilane and monohydroxysilane contained in the reaction solution, that is, with ease of purification.

DESCRIPTION OF THE PREFERRED EMBODIMENTS

Figure 1:
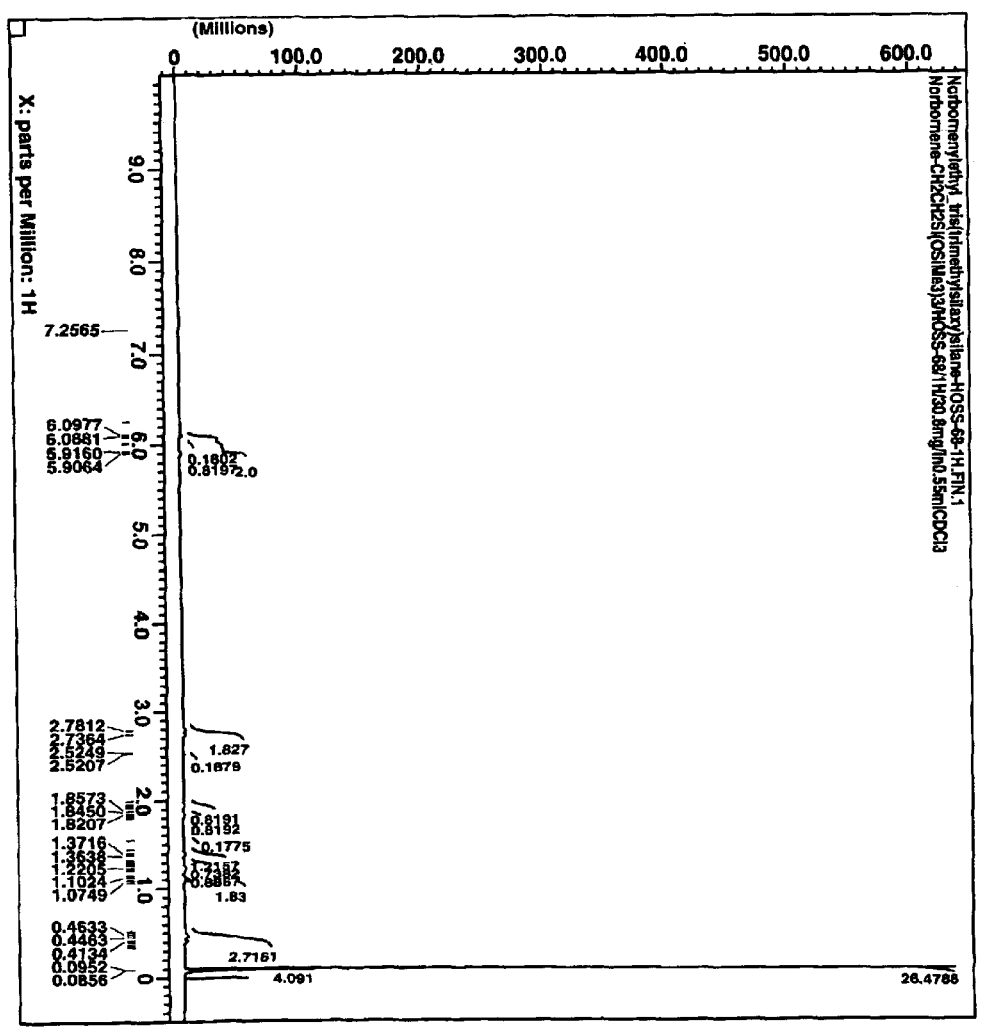
FIGS. 1 and 2 are charts of $^1$H-NMR (in heavy chloroform solvent) and IR spectrum of the product of Example 15, respectively.

According to the inventive method, a branched tetrasiloxane is prepared by reacting a branched siloxane compound of the general formula (2) containing a monoorganoxysilane compound (typically a monoalkoxysilane compound) or a monohydroxysilane compound of the general formula (1) or both as an impurity with a disiloxane compound of the general formula (3) in the presence of an acid compound.

$$R^1_n Si(OSiR^2_3)_{3-n}(OR^3) \tag{1}$$

$$R^1_n Si(OSiR^2_3)_{4-n} \tag{2}$$

$$R^2_3 SiOSiR^2_3 \tag{3}$$

Herein $R^1$ is a substituted or unsubstituted monovalent hydrocarbon group of 1 to 20 carbon atoms, $R^2$ and $R^3$ are selected from hydrogen and substituted or unsubstituted monovalent hydrocarbon groups of 1 to 20 carbon atoms, $R^2$ may be the same or different, and n is equal to 0 or 1.

The branched siloxane compound with which the inventive method starts has the formula (2) wherein $R^1$ is selected from substituted or unsubstituted monovalent hydrocarbon groups of 1 to 20 carbon atoms, preferably 1 to 6 carbon atoms, for example, alkyl groups such as methyl, ethyl, n-propyl, isopropyl, n-butyl, isobutyl, sec-butyl, tert-butyl, n-hexyl, n-octyl, n-decyl, and n-octadecyl, cycloalkyl groups such as cyclopentyl and cyclohexyl, cycloalkenyl groups such as norbornenyl and 2-(5-norbornenyl)ethyl, alkenyl groups such as vinyl and allyl, aryl groups such as phenyl, o-tolyl, p-styryl, m-styryl and o-styryl, aralkyl groups such as benzyl and phenylethyl, and substituted alkyl groups, typically halo-substituted or (meth)acryloxy-substituted alkyl groups such as 3-chloropropyl, 3-iodopropyl, 3-acryloxypropyl and 3-methacryloxypropyl.

$R^2$, which may be the same or different, is selected from hydrogen and substituted or unsubstituted monovalent hydrocarbon groups of 1 to 20 carbon atoms, preferably 1 to 6 carbon atoms. Examples include hydrogen, alkyl groups such as methyl, ethyl, n-propyl, isopropyl, n-butyl, isobutyl, sec-butyl, tert-butyl, n-hexyl, n-octyl, n-decyl, and n-octadecyl, cycloalkyl groups such as cyclopentyl and cyclohexyl, alkenyl groups such as vinyl and allyl, aryl groups such as phenyl and o-tolyl, and aralkyl groups such as benzyl and phenylethyl.

Examples of the branched siloxane compound having formula (2) are given below. Suitable tetrasiloxanes include:
methyltris(trimethylsiloxy)silane,
methyltris(triethylsiloxy)silane,
methyltris(dimethylvinylsiloxy)silane,
methyltris(dimethylsiloxy)silane, ethyltris(trimethylsiloxy)silane,
ethyltris(triethylsiloxy)silane,
ethyltris(dimethylvinylsiloxy)silane,
ethyltris(dimethylsiloxy)silane,
n-propyltris(trimethylsiloxy)silane,
n-propyltris(triethylsiloxy)silane,
n-propyltris(dimethylvinylsiloxy)silane,
n-propyltris(dimethylsiloxy)silane,
n-hexyltris(trimethylsiloxy)silane,
n-hexyltris(triethylsiloxy)silane,
n-hexyltris(dimethylvinylsiloxy)silane,
n-hexyltris(dimethylsiloxy)silane,
n-decyltris(trimethylsiloxy)silane,
n-decyltris(triethylsiloxy)silane,
n-decyltris(dimethylvinylsiloxy)silane,
n-decyltris(dimethylsiloxy)silane,
5-norbornenyltris(trimethylsiloxy)silane,
5-norbornenyltris(triethylsiloxy)silane,
5-norbornenyltris(dimethylvinylsiloxy)silane,
5-norbornenyltris(dimethylsiloxy)silane,
2-(5-norbornenyl)ethyltris(trimethylsiloxy)silane,
2-(5-norbornenyl)ethyltris(triethylsiloxy)silane,
2-(5-norbornenyl)ethyltris(dimethylvinylsiloxy)silane,
2-(5-norbornenyl)ethyltris(dimethylsiloxy)silane,
vinyltris(trimethylsiloxy)silane,
vinyltris(triethylsiloxy)silane,
vinyltris(dimethylvinylsiloxy)silane,
vinyltris(dimethylsiloxy)silane,
allyltris(trimethylsiloxy)silane,
allyltris(triethylsiloxy)silane,
allyltris(dimethylvinylsiloxy)silane,
allyltris(dimethylsiloxy)silane,
phenyltris(trimethylsiloxy)silane,
phenyltris(triethylsiloxy)silane,
phenyltris(dimethylvinylsiloxy)silane,
phenyltris(dimethylsiloxy)silane,
p-styryltris(trimethylsiloxy)silane,
p-styryltris(triethylsiloxy)silane,
p-styryltris(dimethylvinylsiloxy)silane,
p-styryltris(dimethylsiloxy)silane,
m-styryltris(trimethylsiloxy)silane,
m-styryltris(triethylsiloxy)silane,
m-styryltris(dimethylvinylsiloxy)silane,
m-styryltris(dimethylsiloxy)silane,
o-styryltris(trimethylsiloxy)silane,
o-styryltris(triethylsiloxy)silane,
o-styryltris(dimethylvinylsiloxy)silane,
o-styryltris(dimethylsiloxy)silane,
3-chloropropyltris(trimethylsiloxy)silane,
3-chloropropyltris(triethylsiloxy)silane,
3-chloropropyltris(dimethylvinylsiloxy)silane,
3-chloropropyltris(dimethylsiloxy)silane,
3-iodopropyltris(trimethylsiloxy)silane,
3-iodopropyltris(triethylsiloxy)silane,
3-iodopropyltris(dimethylvinylsiloxy)silane,
3-iodopropyltris(dimethylsiloxy)silane,
3-acryloxypropyltris(trimethylsiloxy)silane,
3-acryloxypropyltris(triethylsiloxy)silane,
3-acryloxypropyltris(dimethylvinylsiloxy)silane,
3-acryloxypropyltris(dimethylsiloxy)silane,
3-methacryloxypropyltris(trimethylsiloxy)silane,
3-methacryloxypropyltris(triethylsiloxy)silane,
3-methacryloxypropyltris(dimethylvinylsiloxy)silane,
3-methacryloxypropyltris(dimethylsiloxy)silane, etc.
Suitable pentasiloxanes include
tetrakis(trimethylsiloxy)silane,
tetrakis(triethylsiloxy)silane,
tetrakis(dimethylsiloxy)silane,
tetrakis(dimethylvinylsiloxy)silane, etc.

In the starting branched siloxane compound, a monoorganoxysilane and/or monohydroxysilane having the formula (1) is contained as an impurity.

$R^3$ in formula (1) is selected from hydrogen and substituted or unsubstituted monovalent hydrocarbon groups of 1 to 20 carbon atoms, preferably 1 to 6 carbon atoms. Examples include hydrogen, alkyl groups such as methyl, ethyl, n-propyl, isopropyl, n-butyl, isobutyl, sec-butyl, tert-butyl, n-hexyl, n-octyl, n-decyl, and n-octadecyl, and cycloalkyl groups such as cyclopentyl and cyclohexyl.

The monoorganoxysilane (typically monoalkoxysilane) and monohydroxysilane having the formula (1) corresponds to a branched siloxane compound having the formula (2) wherein one of siloxy groups is replaced by an organoxy group (typically alkoxyl group) or hydroxyl group.

Examples of the monoorganoxysilane and monohydroxysilane having the formula (1) include:
methylbis(trimethylsiloxy)methoxysilane,
methylbis(trimethylsiloxy)ethoxysilane,
methylbis(trimethylsiloxy)silanol,
methylbis(triethylsiloxy)methoxysilane,
methylbis(triethylsiloxy)ethoxysilane,
methylbis(triethylsiloxy)silanol,
methylbis(dimethylvinylsiloxy)methoxysilane,
methylbis(dimethylvinylsiloxy)ethoxysilane,
methylbis(dimethylvinylsiloxy)silanol,
methylbis(dimethylsiloxy)methoxysilane,
methylbis(dimethylsiloxy)ethoxysilane,
methylbis(dimethylsiloxy)silanol,
ethylbis(trimethylsiloxy)methoxysilane,
ethylbis(trimethylsiloxy)ethoxysilane,
ethylbis(trimethylsiloxy)silanol,
ethylbis(triethylsiloxy)methoxysilane,
ethylbis(triethylsiloxy)ethoxysilane,
ethylbis(triethylsiloxy)silanol,
ethylbis(dimethylvinylsiloxy)methoxysilane,
ethylbis(dimethylvinylsiloxy)ethoxysilane,
ethylbis(dimethylvinylsiloxy)silanol,
ethylbis(dimethylsiloxy)methoxysilane,
ethylbis(dimethylsiloxy)ethoxysilane,
ethylbis(dimethylsiloxy)silanol,
n-propylbis(trimethylsiloxy)methoxysilane,
n-propylbis(trimethylsiloxy)ethoxysilane,
n-propylbis(trimethylsiloxy)silanol,
n-propylbis(triethylsiloxy)methoxysilane,
n-propylbis(triethylsiloxy)ethoxysilane,
n-propylbis(triethylsiloxy)silanol,
n-propylbis(dimethylvinylsiloxy)methoxysilane,
n-propylbis(dimethylvinylsiloxy)ethoxysilane,
n-propylbis(dimethylvinylsiloxy)silanol,
n-propylbis(dimethylsiloxy)methoxysilane,
n-propylbis(dimethylsiloxy)ethoxysilane,
n-propylbis(dimethylsiloxy)silanol,
n-hexylbis(trimethylsiloxy)methoxysilane,
n-hexylbis(trimethylsiloxy)ethoxysilane,
n-hexylbis(trimethylsiloxy)silanol,
n-hexylbis(triethylsiloxy)methoxysilane,
n-hexylbis(triethylsiloxy)ethoxysilane,
n-hexylbis(triethylsiloxy)silanol,
n-hexylbis(dimethylvinylsiloxy)methoxysilane,
n-hexylbis(dimethylvinylsiloxy)ethoxysilane,
n-hexylbis(dimethylvinylsiloxy)silanol,
n-hexylbis(dimethylsiloxy)methoxysilane,
n-hexylbis(dimethylsiloxy)ethoxysilane,
n-hexylbis(dimethylsiloxy)silanol, n-decylbis(trimethylsiloxy)methoxysilane,
n-decylbis(trimethylsiloxy)ethoxysilane,
n-decylbis(trimethylsiloxy)silanol,
n-decylbis(triethylsiloxy)methoxysilane,
n-decylbis(triethylsiloxy)ethoxysilane,
n-decylbis(triethylsiloxy)silanol,
n-decylbis(dimethylvinylsiloxy)methoxysilane,
n-decylbis(dimethylvinylsiloxy)ethoxysilane,
n-decylbis(dimethylvinylsiloxy)silanol,
n-decylbis(dimethylsiloxy)methoxysilane,
n-decylbis(dimethylsiloxy)ethoxysilane,
n-decylbis(dimethylsiloxy)silanol,
5-norbornenylbis(trimethylsiloxy)methoxysilane,
5-norbornenylbis(trimethylsiloxy)ethoxysilane,
5-norbornenylbis(trimethylsiloxy)silanol,
5-norbornenylbis(triethylsiloxy)methoxysilane,
5-norbornenylbis(triethylsiloxy)ethoxysilane,
5-norbornenylbis(triethylsiloxy)silanol,
5-norbornenylbis(dimethylvinylsiloxy)methoxysilane,
5-norbornenylbis(dimethylvinylsiloxy)ethoxysilane,
5-norbornenylbis(dimethylvinylsiloxy)silanol,
vinylbis(trimethylsiloxy)methoxysilane,
vinylbis(trimethylsiloxy)ethoxysilane,
vinylbis(trimethylsiloxy)silanol,
vinylbis(triethylsiloxy)methoxysilane,
vinylbis(triethylsiloxy)ethoxysilane,
vinylbis(triethylsiloxy)silanol,
vinylbis(dimethylvinylsiloxy)methoxysilane,
vinylbis(dimethylvinylsiloxy)ethoxysilane,
vinylbis(dimethylvinylsiloxy)silanol,
vinylbis(dimethylsiloxy)methoxysilane,
vinylbis(dimethylsiloxy)ethoxysilane,
vinylbis(dimethylsiloxy)silanol,
allylbis(trimethylsiloxy)methoxysilane,
allylbis(trimethylsiloxy)ethoxysilane,
allylbis(trimethylsiloxy)silanol,
allylbis(triethylsiloxy)methoxysilane,
allylbis(triethylsiloxy)ethoxysilane,
allylbis(triethylsiloxy)silanol,
allylbis(dimethylvinylsiloxy)methoxysilane,
allylbis(dimethylvinylsiloxy)ethoxysilane,
allylbis(dimethylvinylsiloxy)silanol,
allylbis(dimethylsiloxy)methoxysilane,
allylbis(dimethylsiloxy)ethoxysilane,
allylbis(dimethylsiloxy)silanol,
phenylbis(trimethylsiloxy)methoxysilane,
phenylbis(trimethylsiloxy)ethoxysilane,
phenylbis(trimethylsiloxy)silanol,
phenylbis(triethylsiloxy)methoxysilane,
phenylbis(triethylsiloxy)ethoxysilane,
phenylbis(triethylsiloxy)silanol,
phenylbis(dimethylvinylsiloxy)methoxysilane,
phenylbis(dimethylvinylsiloxy)ethoxysilane,
phenylbis(dimethylvinylsiloxy)silanol,
phenylbis(dimethylsiloxy)methoxysilane,
phenylbis(dimethylsiloxy)ethoxysilane,
phenylbis(dimethylsiloxy)silanol,
2-(5-norbornenyl)ethylbis(trimethylsiloxy)methoxysilane,
2-(5-norbornenyl)ethylbis(trimethylsiloxy)ethoxysilane,
2-(5-norbornenyl)ethylbis(trimethylsiloxy)silanol,
2-(5-norbornenyl)ethylbis(dimethylvinylsiloxy) methoxysilane,
2-(5-norbornenyl)ethylbis(dimethylvinylsiloxy) ethoxysilane,
2-(5-norbornenyl)ethylbis(dimethylvinylsiloxy)silanol,
3-chloropropylbis(trimethylsiloxy)methoxysilane,
3-chloropropylbis(trimethylsiloxy)ethoxysilane,
3-chloropropylbis(trimethylsiloxy)silanol,
3-chloropropylbis(triethylsiloxy)methoxysilane,
3-chloropropylbis(triethylsiloxy)ethoxysilane,
3-chloropropylbis(triethylsiloxy)silanol,
3-chloropropylbis(dimethylvinylsiloxy)methoxysilane,
3-chloropropylbis(dimethylvinylsiloxy)ethoxysilane,
3-chloropropylbis(dimethylvinylsiloxy)silanol,
3-chloropropylbis(dimethylsiloxy)methoxysilane,
3-chloropropylbis(dimethylsiloxy)ethoxysilane,
3-chloropropylbis(dimethylsiloxy)silanol,
3-iodopropylbis(trimethylsiloxy)methoxysilane,
3-iodopropylbis(trimethylsiloxy)ethoxysilane,
3-iodopropylbis(trimethylsiloxy)silanol,
3-iodopropylbis(triethylsiloxy)methoxysilane,
3-iodopropylbis(triethylsiloxy)ethoxysilane,
3-iodopropylbis(triethylsiloxy)silanol,
3-iodopropylbis(dimethylvinylsiloxy)methoxysilane,
3-iodopropylbis(dimethylvinylsiloxy)ethoxysilane,
3-iodopropylbis(dimethylvinylsiloxy)silanol,
3-iodopropylbis(dimethylsiloxy)methoxysilane,
3-iodopropylbis(dimethylsiloxy)ethoxysilane,
3-iodopropylbis(dimethylsiloxy)silanol,
3-acryloxypropylbis(trimethylsiloxy)methoxysilane,
3-acryloxypropylbis(trimethylsiloxy)ethoxysilane,
3-acryloxypropylbis(trimethylsiloxy)silanol,
3-acryloxypropylbis(triethylsiloxy)methoxysilane,
3-acryloxypropylbis(triethylsiloxy)ethoxysilane,
3-acryloxypropylbis(triethylsiloxy)silanol,
3-acryloxypropylbis(dimethylvinylsiloxy)methoxysilane,
3-acryloxypropylbis(dimethylvinylsiloxy)ethoxysilane,
3-acryloxypropylbis(dimethylvinylsiloxy)silanol,
3-acryloxypropylbis(dimethylsiloxy)methoxysilane,
3-acryloxypropylbis(dimethylsiloxy)ethoxysilane,
3-acryloxypropylbis(dimethylsiloxy)silanol,
3-methacryloxypropylbis(trimethylsiloxy)methoxysilane,
3-methacryloxypropylbis(trimethylsiloxy)ethoxysilane,
3-methacryloxypropylbis(trimethylsiloxy)silanol,
3-methacryloxypropylbis(triethylsiloxy)methoxysilane,
3-methacryloxypropylbis(triethylsiloxy)ethoxysilane,
3-methacryloxypropylbis(triethylsiloxy)silanol,
3-methacryloxypropylbis(dimethylvinylsiloxy) methoxysilane,
3-methacryloxypropylbis(dimethylvinylsiloxy) ethoxysilane,
3-methacryloxypropylbis(dimethylvinylsiloxy)silanol,
3-methacryloxypropylbis(dimethylsiloxy)methoxysilane,
3-methacryloxypropylbis(dimethylsiloxy)ethoxysilane,
3-methacryloxypropylbis(dimethylsiloxy)silanol,
tris(trimethylsiloxy)methoxysilane,
tris(trimethylsiloxy)ethoxysilane,
tris(trimethylsiloxy)silanol,
tris(triethylsiloxy)methoxysilane,
tris(triethylsiloxy)ethoxysilane,
tris(triethylsiloxy)silanol,
tris(dimethylvinylsiloxy)methoxysilane,
tris(dimethylvinylsiloxy)ethoxysilane,
tris(dimethylvinylsiloxy)silanol,
tris(dimethylsiloxy)methoxysilane,
tris(dimethylsiloxy)ethoxysilane,
tris(dimethylsiloxy)silanol, etc.

The amount of monoorganoxysilane compound and monohydroxysilane compound having the formula (1) contained in the branched siloxane compound having the formula (2) is not particularly limited. There may be contained impurities other than the monoorganoxysilane compound and monohydroxysilane compound having the formula (1).

The disiloxane compound used herein is of the formula (3). $R^2$ in formula (3) is selected from hydrogen and substituted or unsubstituted monovalent hydrocarbon groups of 1 to 20 carbon atoms, preferably 1 to 6 carbon atoms, and may be the same or different. Examples include hydrogen, alkyl groups such as methyl, ethyl, n-propyl, isopropyl, n-butyl, isobutyl, sec-butyl, tert-butyl, n-hexyl, n-octyl, n-decyl, and n-octadecyl, cycloalkyl groups such as cyclopentyl and cyclohexyl, alkenyl groups such as vinyl and allyl, aryl groups such as phenyl and o-tolyl, and aralkyl groups such as benzyl and phenylethyl.

Examples of the disiloxane compound having the formula (3) include hexamethyldisiloxane, hexaethyldisiloxane, hexa-n-propyldisiloxane, 1,3-di-tert-butyl-1,1,3,3-tetramethyldisiloxane, 1,3-divinyl-1,1,3,3-tetramethyldisiloxane, hexaphenyldisiloxane, 1,1,3,3-tetramethyldisiloxane, 1,1,3,3-tetraisopropyldisiloxane, etc.

An appropriate amount of the disiloxane compound used is 0.5 to 200 moles, more preferably 1 to 100 moles, per mole of the monoorganoxysilane compound and monohydroxysilane compound having the formula (1) combined. Outside the range, less amounts of the disiloxane compound may be insufficient to fully reduce the monoorganoxysilane compound and monohydroxysilane compound whereas with more amounts, no further improvement in yield may be expectable and the pot yield may become lower.

The acid compounds used herein include sulfuric acid, hydrochloric acid, methanesulfonic acid, and trifluoromethanesulfonic acid, with sulfuric acid and hydrochloric acid being preferred. An appropriate amount of the acid compound used is 0.1 to 300 moles, more preferably 1 to 30 moles, per mole of the monoorganoxysilane compound and monohydroxysilane compound having the formula (1) combined. Outside the range, less amounts of the acid compound may be ineffective for fully reducing the monoorganoxysilane compound and monohydroxysilane compound whereas with more amounts, no further improvement in yield may be expectable.

According to the invention, the disiloxane compound of formula (3) is added to the branched siloxane compound of formula (2) containing a monoorganoxysilane compound and/or a monohydroxysilane compound as an impurity, after which the acid compound is added for reaction.

The acid compound is added to a liquid mixture of the branched siloxane compound of formula (2) and the disiloxane compound of formula (3) desirably at a temperature of 0 to 100° C., more desirably 15 to 40° C. The reaction time is desirably 0.2 to 10 hours, more desirably 0.5 to 5 hours. When conc. sulfuric acid or conc. hydrochloric acid is used as the acid compound, a layer containing the acid compound can be conveniently removed by separatory operation.

The reaction solution in which reaction with the acid compound has taken place is preferably neutralized with a basic aqueous solution such as aqueous sodium bicarbonate. More preferably, the reaction solution is washed with water and then neutralized with a basic aqueous solution such as aqueous sodium bicarbonate. Further preferably, the organic layer is washed with water again until it becomes neutral. Following water washing, the reaction solution may be dried over a desiccant such as anhydrous sodium sulfate or calcium chloride and then purified by distillation, or directly purified by distillation without adding a desiccant. Distillation may be customarily performed under atmospheric pressure or vacuum, collecting the target branched siloxane.

According to the invention, by reacting a branched siloxane compound of formula (2) containing a monoorganoxysilane compound and/or a monohydroxysilane compound of formula (1) as an impurity with a disiloxane compound of formula (3) in the presence of an acid compound, the branched siloxane compound of formula (2) containing a reduced level of the compound of formula (1) is obtained. Provided that A is the total amount of compounds of formula (1) and B is the amount of the branched siloxane compound of formula (2), both expressed in area percents by gas chromatography, the method starts with the branched siloxane compound of formula (2) containing compounds of formula (1) as impurities so that B/A is generally in the range of 0.1 to 100, preferably 5 to 50, and produces the target branched siloxane compound of formula (2) purified so that B/A is generally in the range of 50 to 100,000, preferably 100 to 5,000. Provided that X is B/A of the starting material and Y is B/A of the purified product, Y/X is preferably in the range of 1.5 to 10,000, more preferably 5 to 1,000.

The (starting) branched siloxane compound of formula (2) containing a monoorganoxysilane compound and/or a monohydroxysilane compound of formula (1) as an impurity can be synthesized by effecting co-hydrolysis of a disiloxane compound of formula (3) and an organoxysilane compound of the general formula (4):

$$R^1{}_n Si(OR^4)_{4-n} \quad (4)$$

wherein $R^1$ is as defined above, $R^4$ is a substituted or unsubstituted monovalent hydrocarbon group of 1 to 20 carbon atoms, and n is equal to 0 or 1, in the presence of an acid catalyst. Preferably, the starting branched siloxane compound of formula (2) is prepared by adding an organoxysilane compound of formula (4) to a liquid mixture of a disiloxane compound of formula (3), an alcohol and the acid catalyst for reaction, and further adding water for effecting co-hydrolysis. However, the starting branched siloxane compound is not limited to those compounds prepared by these procedures.

The organoxysilane compound used herein is of formula (4). $R^1$ in formula (4) is selected from substituted or unsubstituted monovalent hydrocarbon groups of 1 to 20 carbon atoms, preferably 1 to 6 carbon atoms, for example, alkyl groups such as methyl, ethyl, n-propyl, isopropyl, n-butyl, isobutyl, sec-butyl, tert-butyl, n-hexyl, n-octyl, n-decyl, and n-octadecyl, cycloalkyl groups such as cyclopentyl and cyclohexyl, cycloalkenyl groups such as 5-norbornenyl and 2-(5-norbornenyl)ethyl, alkenyl groups such as vinyl and allyl, aryl groups such as phenyl, o-tolyl, p-styryl, m-styryl and o-styryl, aralkyl groups such as benzyl and phenylethyl, and substituted alkyl groups, typically halo-substituted or (meth)acryloxy-substituted alkyl groups such as 3-chloropropyl, 3-iodopropyl, 3-acryloxypropyl and 3-methacryloxypropyl.

$R^4$ in formula (4) is selected from substituted or unsubstituted monovalent hydrocarbon groups of 1 to 20 carbon atoms, preferably 1 to 6 carbon atoms, for example, alkyl groups such as methyl, ethyl, n-propyl, isopropyl, n-butyl, isobutyl, sec-butyl, tert-butyl, n-hexyl, n-octyl, n-decyl, and n-octadecyl, and cycloalkyl groups such as cyclopentyl and cyclohexyl.

Examples of the organoxysilane compound having formula (4) are given below. Suitable trialkoxysilanes include: methyltrimethoxysilane, methyltriethoxysilane, methyltri-n-propoxysilane, methyltriisopropoxysilane, ethyltrimethoxysilane, ethyltriethoxysilane, ethyltri-n-propoxysilane, ethyltriisopropoxysilane, n-propyltrimethoxysilane, n-propyltriethoxysilane, n-propyltri-n-propoxysilane, n-propyltriisopropoxysilane, isopropyltrimethoxysilane, isopropyltriethoxysilane, n-butyltrimethoxysilane, n-butyltriethoxysilane, n-hexyltrimethoxysilane, n-hexyltriethoxysilane,
n-octyltrimethoxysilane, n-octyltriethoxysilane,
n-decyltrimethoxysilane, n-decyltriethoxysilane,
n-octadecyltrimethoxysilane, n-octadecyltriethoxysilane,
5-norbornenyltrimethoxysilane,
5-norbornenyltriethoxysilane,
2-(5-norbornenyl)ethyltrimethoxysilane,
2-(5-norbornenyl)ethyltriethoxysilane,
vinyltrimethoxysilane, vinyltriethoxysilane,
vinyltri-n-propoxysilane, vinyltriisopropoxysilane,
allyltrimethoxysilane, allyltriethoxysilane,
allyltri-n-propoxysilane, allyltriisopropoxysilane,
phenyltrimethoxysilane, phenyltriethoxysilane,
phenyltri-n-propoxysilane, phenyltriisopropoxysilane,
p-styryltrimethoxysilane, p-styryltriethoxysilane,
p-styryltri-n-propoxysilane, p-styryltriisopropoxysilane,
m-styryltrimethoxysilane, m-styryltriethoxysilane,
m-styryltri-n-propoxysilane, m-styryltriisopropoxysilane,
o-styryltrimethoxysilane, o-styryltriethoxysilane,
o-styryltri-n-propoxysilane, o-styryltriisopropoxysilane,
3-chloropropyltrimethoxysilane,
3-chloropropyltriethoxysilane,
3-chloropropyltri-n-propoxysilane,
3-chloropropyltriisopropoxysilane,
3-iodopropyltrimethoxysilane, 3-iodopropyltriethoxysilane,
3-iodopropyltri-n-propoxysilane,
3-iodopropyltriisopropoxysilane,
3-acryloxypropyltrimethoxysilane,
3-acryloxypropyltriethoxysilane,
3-acryloxypropyltri-n-propoxysilane,
3-acryloxypropyltriisopropoxysilane,
3-methacryloxypropyltrimethoxysilane,
3-methacryloxypropyltriethoxysilane,
3-methacryloxypropyltri-n-propoxysilane,
3-methacryloxypropyltriisopropoxysilane, etc.

Suitable tetraalkoxysilanes include: tetramethoxysilane, tetraethoxysilane, tetra-n-propoxysilane, tetraisopropoxysilane, tetra-n-butoxysilane, etc.

Any organoxysilane compounds synthesized by conventional methods may be used after purification. Also a reaction solution synthesized by de-hydrochlorination reaction of a chlorosilane with an alcohol may be used without purification. The chlorosilane used for synthesis of the organoxysilane compounds is a compound of formula (4) wherein the organoxy groups such as alkoxyl are replaced by chloro. Examples of the chlorosilane include trichlorosilanes such as methyltrichlorosilane, ethyltrichlorosilane, n-propyltrichlorosilane, isopropyltrichlorosilane, n-butyltrichlorosilane, n-hexyltrichlorosilane, n-octyltrichlorosilane, n-decyltrichlorosilane, n-octadecyltrichlorosilane, 5-norbornenyltrichlorosilane, 2-(5-norbornenyl)ethyltrichlorosilane, vinyltrichlorosilane, allyltrichlorosilane, phenyltrichlorosilane, p-styryltrichlorosilane, m-styryltrichlorosilane, o-styryltrichlorosilane, 3-chloropropyltrichlorosilane, 3-acryloxypropyltrichlorosilane, 3-methacryloxypropyltrichlorosilane, etc. and tetrachlorosilane. Examples of the alcohol to be reacted with the chlorosilane include methanol, ethanol, n-propanol, isopropanol, n-butanol, and isobutanol. Of these, methanol, ethanol and isopropanol are preferred. An unpurified organoxysilane compound resulting from de-hydrochlorination reaction of a chlorosilane with an alcohol generally has a high purity and contains alcohol and a minor amount of disiloxane as impurities. The unpurified organoxysilane compound can be used herein as long as its purity is at least 50%, although a purity of at least 80%, especially at least 90% is preferred.

An appropriate amount of the disiloxane compound having formula (3) used is 1.5 to 10 moles, more preferably 1.5 to 4 moles, per mole of the organoxysilane compound having formula (4). With less than 1.5 moles of the disiloxane compound, the yield of branched siloxane may become lower. With more than 10 moles, the pot yield may become lower.

An appropriate amount of the alcohol used is 0.5 to 5 moles, more preferably 1 to 3 moles, per mole of the organoxysilane compound having formula (4). With less than 0.5 mole of the alcohol, the yield of branched siloxane may become lower. With more than 5 moles, the pot yield may become lower.

The acid catalysts used herein include sulfuric acid, hydrochloric acid, methanesulfonic acid, and trifluoromethanesulfonic acid, with sulfuric acid and trifluoromethanesulfonic acid being preferred. An appropriate amount of the acid catalyst used is 0.001 to 0.5 mole, more preferably 0.01 to 0.2 mole, per mole of the organoxysilane compound having the formula (4). Less than 0.001 mole of the acid catalyst may provide a slower reaction rate and require a longer reaction time.

Water used for the hydrolysis reaction may be water alone or in admixture with an alcohol. An appropriate amount of water used is 1 to 50 moles, more preferably 1.5 to 20 moles, and even more preferably 2 to 8 moles, per mole of the organoxysilane compound having formula (4). Outside the range, less amounts of water may not allow reaction to take place to a full extent, resulting in reduced yields. With more amounts, no further improvement in yield may be expectable and the pot yield may become lower. The amount of alcohol, if used, is preferably less than the moles of water used. The alcohol used is typically selected from among methanol, ethanol, n-propanol, isopropanol, n-butanol and isobutanol and is preferably the same as the alcohol used along with the disiloxane compound having formula (3).

In the preferred embodiment, the starting branched siloxane compound of formula (2) is prepared by adding an organoxysilane compound of formula (4) to a liquid mixture of a disiloxane compound of formula (3), an alcohol and the acid catalyst for effecting reaction, and further adding water for effecting co-hydrolysis. It is possible to add an organoxysilane compound to a liquid mixture of a disiloxane compound and an alchol for effecting reaction prior to addition of an acid catalyst. In this case, however, if the organoxysilane compound of formula (4) is methyltrimethoxysilane or the like, high-molecular weight siloxanes can form as by-products to reduce the yield of the target branched siloxane. The disiloxane compound, alcohol and acid catalyst may be mixed in any desired order, although it is preferred to add an acid catalyst to a liquid mixture of disiloxane compound and alcohol.

The acid catalyst is added to a liquid mixture of the disiloxane compound of formula (3) and the alcohol desirably at a temperature of 0 to 100° C., more desirably 5 to 40° C. The reaction time is desirably 0.1 to 5 hours, more desirably 0.5 to 2 hours. The organoxysilane compoud having formula (4) is added to the resulting reaction solution desirably at a temperature of 0 to 100° C., more desirably 5 to 70° C. The reaction time is desirably 0.5 to 8 hours, more desirably 0.5 to 3 hours. With water added to the reaction solution, co-hydrolysis is performed desirably at a temperature of 1 to 100° C., more desirably 1 to 70° C. At lower temperatures, water will freeze. At higher temperatures, the once produced branches siloxane is converted into a high-molecular weight siloxane through redistribution reaction, resulting in a reduced yield of the target branched siloxane.

The reaction time is desirably 0.5 to 15 hours, more desirably 1 to 7 hours.

The reaction may be performed in a solventless system although a solvent may be used. Suitable solvents, if used, include hydrocarbon solvents such as hexane, cyclohexane, heptane, octane, isooctane, dodecane, benzene, toluene and xylene, and ether solvents such as tetrahydrofuran and dioxane.

By the procedure described above, the branched siloxane compound of formula (2) containing a monoorganoxysilane compound and/or a monohydroxysilane compound as an impurity is obtained. The resulting reaction solution may be used as such in the inventive method. Alternatively, the reaction solution is distilled to collect a fraction of the branched siloxane compound of formula (2) containing a monoorganoxysilane compound and/or a monohydroxysilane compound as an impurity, which may be used in the inventive method. In the former embodiment wherein the reaction solution is used as such, a disiloxane compound is used in excess relative to the theory for reaction to take place. If unreacted disiloxane compound is contained, it becomes unnecessary to add the disiloxane compound again prior to reaction with an acid compound, although it is acceptable to add the disiloxane compound again. The level of monoorganoxysilane compound and monohydroxysilane compound in the reaction solution or distilled fraction can be determined by suitable analysis such as gas chromatography (GC).

EXAMPLE

Examples and Comparative Examples are given below for illustrating the invention although the invention is not limited thereto.

In Examples, abbreviations are: Me for methyl, n-Pr for n-propyl, Vi for vinyl, 3-MAP for 3-methacryloxypropyl, 3-AP for 3-acryloxypropyl, ST for p-styryl, and NBE for 2-(5-norbornenyl)ethyl.

Example 1

A 200-ml four necked glass flask equipped with a reflux condenser, thermometer and stirrer was purged with nitrogen. The flask was charged with 100 g of a liquid mixture containing 61.9% of hexamethyldisiloxane, 32.0% of methyltris(trimethylsiloxy)silane, 5.4% of MeSi(OMe)(OSiMe$_3$)$_2$ (monomethoxy compound), and 0.7% of MeSi(OH)(OSiMe$_3$)$_2$ (monohydroxy compound), as expressed in area percents by GC. In the mixture, the area percent ratio of methyltris(trimethylsiloxy)silane to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 5.28. The total content of monomethoxy and monohydroxy compounds was 0.024 mol, as determined from the area percents by GC.

To the mixture was added 3.6 g (0.037 mol) of conc. sulfuric acid. The mixture was stirred at 20–25° C. for 3 hours. On GC analysis, the reaction solution was found to contain 59.9% of hexamethyldisiloxane, 39.6% of methyltris(trimethylsiloxy)silane, 0.02% of MeSi(OMe)(OSiMe$_3$)$_2$, and 0% of MeSi(OH)(OSiMe$_3$)$_2$, as expressed in area percents by GC. The area percent ratio of methyltris(trimethylsiloxy)silane to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 2391.8, indicating a substantial loss of monomethoxysilane and monohydroxysilane which were contained in the mixture prior to sulfuric acid treatment. On the other hand, high-molecular weight siloxanes resulting from conc. sulfuric acid-catalyzed redistribution reaction of methyltris(trimethylsiloxy)silane were little detected.

Example 2

A 1000-ml four necked glass flask equipped with a reflux condenser, thermometer and stirrer was purged with nitrogen. The flask was charged with 324.8 g (2.0 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 136.2 g (1.0 mol) of methyltrimethoxysilane was added dropwise over 30 minutes, and stirring was continued at the temperature for one hour. At an internal temperature of 5–25° C., 105.0 g (5.8 mol) of water was added dropwise over one hour. After the completion of dropwise addition, stirring was continued at 15–25° C. for 3 hours. The organic layer of the reaction solution was analyzed by GC, finding that the area percent ratio of the main product to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 33.7. The total content of monomethoxy and monohydroxy compounds was 0.032 mol, as determined from the area percents by GC.

The reaction solution was subjected to separatory operation to remove the aqueous layer. While the organic layer was kept at a temperature of 20–25° C., 14.7 g (0.15 mol) of conc. sulfuric acid was added dropwise over 15 minutes, and stirring was continued at the temperature for 45 minutes. The organic layer after reaction with sulfuric acid was analyzed by GC, finding that the area percent ratio of the main product to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 1010.6. The sulfuric acid layer was removed from the reaction solution, after which the organic layer was washed with water, neutralized with aqueous sodium bicarbonate, and washed with water again. On distillation of the resulting organic layer, 284.3 g (0.92 mol) of methyltris(trimethylsiloxy)silane with a purity of 99.6% was collected as a fraction having a boiling point of 120.0–120.5° C./12 kPa. The yield was 91.5%.

Example 3

A 2000-ml four necked glass flask equipped with a reflux condenser, thermometer and stirrer was purged with nitrogen. The flask was charged with 649.6 g (4.0 mol) of hexamethyldisiloxane and 128.0 g (4.0 mol) of methanol, and cooled in an ice water bath to an internal temperature below 10° C. To the flask kept at an internal temperature of 5–10° C., 19.6 g (0.2 mol) of conc. sulfuric acid was added dropwise over 30 minutes, and stirring was continued at the temperature for 30 minutes. Subsequently, to the flask kept at an internal temperature of 5–10° C., 283.5 g (2.0 mol of pure methyltrimethoxysilane) of unpurified methyltrimethoxysilane with a purity of 96.1%, which was synthesized by de-hydrochlorination reaction of methyltrichlorosilane with methanol, was added dropwise over 45 minutes, and stirring was continued at the temperature for one hour. At an internal temperature of 5–25° C., 209.9 g (11.7 mol) of water was added dropwise over one hour. After the completion of dropwise addition, stirring was continued at 15–25° C. for 3 hours. The organic layer of the reaction solution was analyzed by GC, finding that the area percent ratio of the main product to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 34.0. The total content of monomethoxy and monohydroxy compounds was 0.066 mol, as determined from the area percents by GC.

The reaction solution was subjected to separatory operation to remove the aqueous layer. While the organic layer was kept at a temperature of 20–25° C., 39.2 g (0.4 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 917.1. The sulfuric acid layer was removed from the reaction solution, after which the organic layer was washed with water, neutralized with aqueous sodium bicarbonate, and washed with water again. On distillation of the resulting organic layer, 577.2 g (1.86 mol) of methyltris(trimethylsiloxy)silane with a purity of 99.8% was collected as a fraction having a boiling point of 120.0–120.5° C./12 kPa. The yield was 92.9%.

Example 4

A 1000-ml four necked glass flask equipped with a reflux condenser, thermometer and stirrer was purged with nitrogen. The flask was charged with 324.8 g (2.0 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 164.3 g (1.0 mol) of n-propyltrimethoxysilane was added dropwise over 45 minutes, and stirring was continued at the temperature for one hour. At an internal temperature of 5–25° C., 105.0 g (5.8 mol) of water was added dropwise over one hour. After the completion of dropwise addition, stirring was continued at 20–25° C. for 2 hours and then at 50–55° C. for 2 hours. The organic layer of the reaction solution was analyzed by GC, finding that the area percent ratio of the main product to monomethoxy and monohydroxy compounds, n-PrSi(OSiMe$_3$)$_3$/[n-PrSi(OMe)(OSiMe$_3$)$_2$+n-PrSi(OH)(OSiMe$_3$)$_2$] was 17.9. The total content of monomethoxy and monohydroxy compounds was 0.060 mol, as determined from the area percents by GC.

The reaction solution was subjected to separatory operation to remove the aqueous layer. While the organic layer was kept at a temperature of 20–25° C., 24.5 g (0.25 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, n-PrSi(OSiMe$_3$)$_3$/[n-PrSi(OMe)(OSiMe$_3$)$_2$+n-PrSi(OH)(OSiMe$_3$)$_2$] was 1663.2. The sulfuric acid layer was removed from the reaction solution, after which the organic layer was washed with water, neutralized with aqueous sodium bicarbonate, and washed with water again. On distillation of the resulting organic layer, 317.8 g (0.94 mol) of n-propyltris(trimethylsiloxy)silane with a purity of 99.6% was collected as a fraction having a boiling point of 93.5–94.0° C./1.3 kPa. The yield was 93.8%.

Example 5

A 1000-ml four necked glass flask equipped with a reflux condenser, thermometer and stirrer was purged with nitrogen. The flask was charged with 324.8 g (2.0 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 206.4 g (1.0 mol) of n-hexyltrimethoxysilane was added dropwise over 30 minutes, and stirring was continued at the temperature for one hour. At an internal temperature of 5–25° C., 54.0 g (3.0 mol) of water was added dropwise over one hour. After the completion of dropwise addition, stirring was continued at 15–25° C. for 5 hours. The organic layer of the reaction solution was analyzed by GC, finding that the area percent ratio of the main product to monomethoxy and monohydroxy compounds, n-C$_6$H$_{13}$Si(OSiMe$_3$)$_3$/[n-C$_6$H$_{13}$Si(OMe)(OSiMe$_3$)$_2$+n-C$_6$H$_{13}$Si(OH)(OSiMe$_3$)$_2$] was 19.3. The total content of monomethoxy and monohydroxy compounds was 0.055 mol, as determined from the area percents by GC.

The reaction solution was subjected to separatory operation to remove the aqueous layer. While the organic layer was kept at a temperature of 20–25° C., 24.5 g (0.25 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, n-C$_6$H$_{13}$Si(OSiMe$_3$)$_3$/[n-C$_6$H$_{13}$Si(OMe)(OSiMe$_3$)$_2$+n-C$_6$H$_{13}$Si(OH)(OSiMe$_3$)$_2$] was 4886.4. The sulfuric acid layer was removed from the reaction solution, after which the organic layer was washed with water, neutralized with aqueous sodium bicarbonate, and washed with water again. On distillation of the resulting organic layer, 363.7 g (0.96 mol) of n-hexyltris(trimethylsiloxy)silane with a purity of 99.3% was collected as a fraction having a boiling point of 103.5–104.5° C./0.4 kPa. The yield was 95.5%.

Example 6

A 1000-ml four necked glass flask equipped with a reflux condenser, thermometer and stirrer was purged with nitrogen. The flask was charged with 324.8 g (2.0 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 262.5 g (1.0 mol) of n-decyltrimethoxysilane was added dropwise over 30 minutes, and stirring was continued at the temperature for one hour. At an internal temperature of 5–25° C., 72.0 g (4.0 mol) of water was added dropwise over one hour. After the completion of dropwise addition, stirring was continued at 15–25° C. for 7 hours. The organic layer of the reaction solution was analyzed by GC, finding that the area percent ratio of the main product to monomethoxy and monohydroxy compounds, n-C$_{10}$H$_{21}$Si(OSiMe$_3$)$_3$/[n-C$_{10}$H$_{21}$Si(OMe)(OSiMe$_3$)$_2$+n-C$_{10}$H$_{21}$Si(OH)(OSiMe$_3$)$_2$] was 5.7. The total content of monomethoxy and monohydroxy compounds was 0.183 mol, as determined from the area percents by GC.

The reaction solution was subjected to separatory operation to remove the aqueous layer. While the organic layer was kept at a temperature of 20–25° C., 49.1 g (0.5 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, n-C$_{10}$H$_{21}$Si(OSiMe$_3$)$_3$/[n-C$_{10}$H$_{21}$Si(OMe)(OSiMe$_3$)$_2$+n-C$_{10}$H$_{21}$Si(OH)(OSiMe$_3$)$_2$] was 129.6. The sulfuric acid layer was removed from the reaction solution, after which the organic layer was washed with water, neutralized with aqueous sodium bicarbonate, and washed with water again. On distillation of the resulting organic layer, 407.1 g (0.93 mol) of n-decyltris(trimethylsiloxy)silane with a purity of 98.4% was collected as a fraction having a boiling point of 140.0–141.5° C./0.3 kPa. The yield was 93.1%.

Example 7

A 1000-ml four necked glass flask equipped with a reflux condenser, thermometer and stirrer was purged with nitrogen. The flask was charged with 372.8 g (2.0 mol) of 1,3-divinyl-1,1,3,3-tetramethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 136.2 g (1.0 mol) of methyltrimethoxysilane was added dropwise over 30 minutes, and stirring was continued at the temperature for one hour. At an internal temperature of 5–25° C., 105.0 g (5.8 mol) of water was added dropwise over one hour. After the completion of dropwise addition, stirring was continued at 15–25° C. for 2.5 hours. The organic layer of the reaction solution was analyzed by GC, finding that the area percent ratio of the main product to monomethoxy and monohydroxy compounds, MeSi(OSiMe$_2$Vi)$_3$/[MeSi(OMe)(OSiMe$_2$Vi)$_2$+MeSi(OH)(OSiMe$_2$Vi)$_2$] was 13.2. The total content of monomethoxy and monohydroxy compounds was 0.074 mol, as determined from the area percents by GC.

The reaction solution was subjected to separatory operation to remove the aqueous layer. While the organic layer was kept at a temperature of 20–25° C., 34.3 g (0.35 mol) of conc. sulfuric acid was added dropwise over 15 minutes, and stirring was continued at the temperature for 0.5 hour. The organic layer after reaction with sulfuric acid was analyzed by GC, finding that the area percent ratio of the main product to monomethoxy and monohydroxy compounds, MeSi(OSiMe$_2$Vi)$_3$/[MeSi(OMe)(OSiMe$_2$Vi)$_2$+MeSi(OH)(OSiMe$_2$Vi)$_2$] was 2990.7. The sulfuric acid layer was removed from the reaction solution, after which the organic layer was washed with water, neutralized with aqueous sodium bicarbonate, and washed with water again. On distillation of the resulting organic layer, 275.3 g (0.79 mol) of methyltris(dimethylvinylsiloxy)silane with a purity of 99.7% was collected as a fraction having a boiling point of 95.0–96.5° C./0.9 kPa. The yield was 79.4%.

Example 8

A 1000-ml four necked glass flask equipped with a reflux condenser, thermometer and stirrer was purged with nitrogen. The flask was charged with 324.8 g (2.0 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 148.2 g (1.0 mol) of vinyltrimethoxysilane was added dropwise over 30 minutes, and stirring was continued at the temperature for one hour. At an internal temperature of 5–25° C., 72.0 g (4.0 mol) of water was added dropwise over one hour. After the completion of dropwise addition, stirring was continued at 15–25° C. for 3 hours. The organic layer of the reaction solution was analyzed by GC, finding that the area percent ratio of the main product to monomethoxy and monohydroxy compounds, ViSi(OSiMe$_3$)$_3$/[ViSi(OMe)(OSiMe$_3$)$_2$+ViSi(OH)(OSiMe$_3$)$_2$] was 29.2. The total content of monomethoxy and monohydroxy compounds was 0.037 mol, as determined from the area percents by GC.

The reaction solution was subjected to separatory operation to remove the aqueous layer. While the organic layer was kept at a temperature of 20–25° C., 19.4 g (0.2 mol) of conc. sulfuric acid was added dropwise over 15 minutes, and stirring was continued at the temperature for 45 minutes. The organic layer after reaction with sulfuric acid was analyzed by GC, finding that the area percent ratio of the main product to monomethoxy and monohydroxy compounds, ViSi(OSiMe$_3$)$_3$/[ViSi(OMe)(OSiMe$_3$)$_2$+ViSi(OH)(OSiMe$_3$)$_2$] was 3938.6. The sulfuric acid layer was removed from the reaction solution, after which the organic layer was washed with water, neutralized with aqueous sodium bicarbonate, and washed with water again. On distillation of the resulting organic layer, 301.8 g (0.94 mol) of vinyltris(trimethylsiloxy)silane with a purity of 99.7% was collected as a fraction having a boiling point of 95.0–96.5° C./0.9 kPa. The yield was 93.5%.

Example 9

A 1000-ml four necked glass flask equipped with a reflux condenser, thermometer and stirrer was purged with nitrogen. The flask was charged with 406.0 g (2.5 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 248.4 g (1.0 mol) of 3-methacryloxypropyltrimethoxysilane was added dropwise over 30 minutes, and stirring was continued at the temperature for one hour. At an internal temperature of 5–25° C., 72.0 g (4.0 mol) of water was added dropwise over one hour. After the completion of dropwise addition, stirring was continued at 15–25° C. for 6.5 hours. The reaction solution was subjected to separatory operation to remove the aqueous layer. The organic layer was washed with water and separated again. The resulting organic layer of the reaction solution was analyzed by GC, finding that the area percent ratio of the main product to monomethoxy and monohydroxy compounds, 3-MAPSi(OSiMe$_3$)$_3$/[3-MAPSi(OMe)(OSiMe$_3$)$_2$+3-MAPSi(OH)(OSiMe$_3$)$_2$] was 22.5. The total content of monomethoxy and monohydroxy compounds was 0.044 mol, as determined from the area percents by GC.

While the organic layer was kept at a temperature of 20–25° C., 24.5 g (0.25 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, 3-MAPSi(OSiMe$_3$)$_3$/[3-MAPSi(OMe)(OSiMe$_3$)$_2$+3-MAPSi(OH)(OSiMe$_3$)$_2$] was 358.3. The sulfuric acid layer was removed from the reaction solution, after which the organic layer was washed with water, neutralized with aqueous sodium bicarbonate, and washed with water again. On distillation of the resulting organic layer, 393.5 g (0.93 mol) of 3-methacryloxypropyltris(trimethylsiloxy)silane with a purity of 99.6% was collected as a fraction having a boiling point of 118.5–120.5° C./0.2 kPa. The yield was 93.1%.

Example 10

A 1000-ml four necked glass flask equipped with a reflux condenser, thermometer and stirrer was purged with nitrogen. The flask was charged with 406.0 g (2.5 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 234.3 g (1.0 mol) of 3-acryloxypropyltrimethoxysilane was added dropwise over 30 minutes, and stirring was continued at the temperature for one hour. At an internal temperature of 5–25° C., 72.0 g (4.0 mol) of water was added dropwise over one hour. After the completion of dropwise addition, stirring was continued at 15–25° C. for 4.5 hours. The reaction solution was subjected to separatory operation to remove the aqueous layer. The organic layer was washed with water and separated again. The resulting organic layer of the reaction solution was analyzed by GC, finding that the area percent ratio of the main product to monomethoxy and monohydroxy compounds, 3-APSi(OSiMe$_3$)$_3$/[3-APSi(OMe)(OSiMe$_3$)$_2$+3-APSi(OH)(OSiMe$_3$)$_2$] was 21.1. The total content of monomethoxy and monohydroxy compounds was 0.046 mol, as determined from the area percents by GC.

While the organic layer was kept at a temperature of 20–25° C., 24.5 g (0.25 mol) of conc. sulfuric acid was added dropwise over 15 minutes, and stirring was continued at the temperature for 30 minutes. The organic layer after reaction with sulfuric acid was analyzed by GC, finding that the area percent ratio of the main product to monomethoxy and monohydroxy compounds, 3-APSi(OSiMe$_3$)$_3$/[3-APSi(OMe)(OSiMe$_3$)$_2$+3-APSi(OH)(OSiMe$_3$)$_2$] was 702.1. The sulfuric acid layer was removed from the reaction solution, after which the organic layer was washed with water, neutralized with aqueous sodium bicarbonate, and washed with water again. On distillation of the resulting organic layer, 380.0 g (0.93 mol) of 3-acryloxypropyltris(trimethylsiloxy)silane with a purity of 98.6% was collected as a fraction having a boiling point of 102.0–104.0° C./0.2 kPa. The yield was 93.0%.

Example 11

A 2000-ml four necked glass flask equipped with a reflux condenser, thermometer and stirrer was purged with nitrogen. The flask was charged with 757.7 g (4.05 mol) of hexamethyldisiloxane and 96.0 g (3.0 mol) of methanol, and cooled in an ice water bath to an internal temperature below 10° C. To the flask kept at an internal temperature of 5–10° C., 14.7 g (0.15 mol) of conc. sulfuric acid was added dropwise over 30 minutes, and stirring was continued at the temperature for 30 minutes. Subsequently, to the flask kept at an internal temperature of 5–10° C., 228.3 g (1.5 mol) of tetramethoxysilane was added dropwise over 30 minutes, and stirring was continued at the temperature for one hour. At an internal temperature of 5–25° C., 108.0 g (6.0 mol) of water was added dropwise over one hour. After the completion of dropwise addition, stirring was continued at 15–25° C. for 6 hours. The organic layer of the reaction solution was analyzed by GC, finding that the area percent ratio of the main product to monomethoxy and monohydroxy compounds, Si(OSiMe$_3$)$_4$/[Si(OMe)(OSiMe$_3$)$_3$+Si(OH)(OSiMe$_3$)$_3$] was 17.2. The total content of monomethoxy and monohydroxy compounds was 0.057 mol, as determined from the area percents by GC.

While the organic layer was kept at a temperature of 20–25° C., 34.3 g (0.35 mol) of conc. sulfuric acid was added dropwise over 15 minutes, and stirring was continued at the temperature for 45 minutes. The organic layer after reaction with sulfuric acid was analyzed by GC, finding that the area percent ratio of the main product to monomethoxy and monohydroxy compounds, Si(OSiMe$_3$)$_4$/[Si(OMe)(OSiMe$_3$)$_3$+Si(OH)(OSiMe$_3$)$_3$] was 2787.4. The sulfuric acid layer was removed from the reaction solution, after which the organic layer was washed with water, neutralized with aqueous sodium bicarbonate, and washed with water again. On distillation of the resulting organic layer, 545.7 g (1.42 mol) of tetrakis(trimethylsiloxy)silane with a purity of 99.6% was collected as a fraction having a boiling point of 109.0–110.0° C./2.7 kPa. The yield was 94.5%.

Example 12

A 1000-ml four necked glass flask equipped with a reflux condenser, thermometer and stirrer was purged with nitrogen. The flask was charged with 324.8 g (2.0 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 136.2 g (1.0 mol) of methyltrimethoxysilane was added dropwise over 30 minutes, and stirring was continued at the temperature for one hour. At an internal temperature of 5–25° C., 105.0 g (5.8 mol) of water was added dropwise over one hour. After the completion of dropwise addition, stirring was continued at 15–25° C. for 3 hours. The organic layer of the reaction solution was analyzed by GC, finding that the area percent ratio of the main product to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 32.7. The total content of monomethoxy and monohydroxy compounds was 0.033 mol, as determined from the area percents by GC.

The reaction solution was subjected to separatory operation to remove the aqueous layer. While the organic layer was kept at a temperature of 20–25° C., 416.7 g (4 mol) of 35% hydrochloric acid was added dropwise over 15 minutes, and stirring was continued at the temperature for 1.8 hours. The organic layer after reaction with 35% hydrochloric acid was analyzed by GC, finding that the area percent ratio of the main product to monomethoxy and monohydroxy compounds, MeSi(OSiMe$_3$)$_3$/[MeSi(OMe)(OSiMe$_3$)$_2$+MeSi(OH)(OSiMe$_3$)$_2$] was 801.6. The hydrochloric acid layer was removed from the reaction solution, after which the organic layer was washed with water, neutralized with aqueous sodium bicarbonate, and washed with water again. On distillation of the resulting organic layer, 282.7 g (0.91 mol) of methyltris(trimethylsiloxy)silane with a purity of 99.5% was collected as a fraction having a boiling point of 120.0–120.5° C./12 kPa. The yield was 91.0%.

Example 13

A 1000-ml four necked glass flask equipped with a reflux condenser, thermometer and stirrer was purged with nitrogen. The flask was charged with 406.0 g (2.5 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 30 minutes, and stirring was continued at the temperature for 30 minutes. Subsequently, to the flask kept at an internal temperature of 5–10° C., 224.3 g (1.0 mol) of p-styryltrimethoxysilane was added dropwise over 30 minutes, and stirring was continued at the temperature for one hour. At an internal temperature of 5–25° C., 72.0 g (4.0 mol) of water was added dropwise over one hour. After the completion of dropwise addition, stirring was continued at 15–25° C. for 6 hours. The organic layer of the reaction solution was analyzed by GC, finding that the area percent ratio of the main product to monomethoxy and monohydroxy compounds, ST-Si(OSiMe$_3$)$_3$/[ST-Si(OMe)(OSiMe$_3$)$_2$ +ST-Si(OH)(OSiMe$_3$)$_2$] was 29.2. The total content of monomethoxy and monohydroxy compounds was 0.035 mol, as determined from the area percents by GC.

The reaction solution was subjected to separatory operation to remove the aqueous layer. While the organic layer was kept at a temperature of 20–25° C., 19.6 g (0.2 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, ST-Si(OSiMe$_3$)$_3$/[ST-Si(OMe)(OSiMe$_3$)$_2$+ST-Si(OH)(OSiMe$_3$)$_2$] was 803.2. The sulfuric acid layer was removed from the reaction solution, after which the organic layer was washed with water, neutralized with aqueous sodium bicarbonate, and washed with water again. On distillation of the resulting organic layer, 357.9 g (0.9 mol) of p-styryltris(trimethylsiloxy)silane with a purity of 99.4% was collected as a fraction having a boiling point of 90.0–92.0° C./0.1 kPa. The yield was 89.7%.

Example 14

A 1000-ml four necked glass flask equipped with a reflux condenser, thermometer and stirrer was purged with nitrogen. The flask was charged with 251.6 g (1.35 mol) of 1,3-divinyl-1,1,3,3-tetramethyldisiloxane and 32.0 g (1.0 mol) of methanol, and cooled in an ice water bath to an internal temperature below 10° C. To the flask kept at an internal temperature of 5–10° C., 4.9 g (0.05 mol) of conc. sulfuric acid was added dropwise over 30 minutes, and stirring was continued at the temperature for 30 minutes. Subsequently, to the flask kept at an internal temperature of 5–10° C., 76.1 g (0.5 mol) of tetramethoxysilane was added dropwise over 30 minutes, and stirring was continued at the temperature for one hour. At an internal temperature of 5–25° C., 48.6 g (2.7 mol) of water was added dropwise over one hour. After the completion of dropwise addition, stirring was continued at 50–55° C. for 5 hours. The organic layer of the reaction solution was analyzed by GC, finding that the area percent ratio of the main product to monomethoxy and monohydroxy compounds, Si(OSiMe$_2$Vi)$_4$/[Si(OMe)(OSiMe$_2$Vi)$_3$+Si(OH)(OSiMe$_2$Vi)$_3$] was 11.1. The total content of monomethoxy and monohydroxy compounds was 0.035 mol, as determined from the area percents by GC.

The reaction solution was subjected to separatory operation to remove the aqueous layer. While the organic layer was kept at a temperature of 20–25° C., 19.6 g (0.2 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, Si(OSiMe$_2$Vi)$_4$/[Si(OMe)(OSiMe$_2$Vi)$_3$+Si(OH)(OSiMe$_2$Vi)$_3$] was 441.2. The sulfuric acid layer was removed from the reaction solution, after which the organic layer was washed with water, neutralized with aqueous sodium bicarbonate, and washed with water again. On distillation of the resulting organic layer, 161.0 g (0.37 mol) of tetrakis(dimethylvinylsiloxy)silane with a purity of 98.9% was collected as a fraction having a boiling point of 105.0–107.0° C./0.5 kPa. The yield was 74.3%.

Example 15

A 1000-ml four necked glass flask equipped with a reflux condenser, thermometer and stirrer was purged with nitrogen. The flask was charged with 389.8 g (2.4 mol) of hexamethyldisiloxane and 51.2 g (1.6 mol) of methanol, and cooled in an ice water bath to an internal temperature below 10° C. To the flask kept at an internal temperature of 5–10° C., 7.84 g (0.08 mol) of conc. sulfuric acid was added dropwise over 30 minutes, and stirring was continued at the temperature for 30 minutes. Subsequently, to the flask kept at an internal temperature of 5–10° C., 193.9 g (0.8 mol) of 2-(5-norbornenyl)ethyltrimethoxysilane was added dropwise over 30 minutes, and stirring was continued at the temperature for one hour. At an internal temperature of 5–25° C., 57.6 g (3.2 mol) of water was added dropwise over one hour. After the completion of dropwise addition, stirring was continued at 50–55° C. for 5 hours. The organic layer of the reaction solution was analyzed by GC, finding that the area percent ratio of the main product to monomethoxy and monohydroxy compounds, NBE-Si(OSiMe$_3$)$_3$/[NBE-Si(OMe)(OSiMe$_3$)$_2$+NBE-Si(OH)(OSiMe$_3$)$_2$] was 20.4. The total content of monomethoxy and monohydroxy compounds was 0.05 mol, as determined from the area percents by GC.

Figure 2:
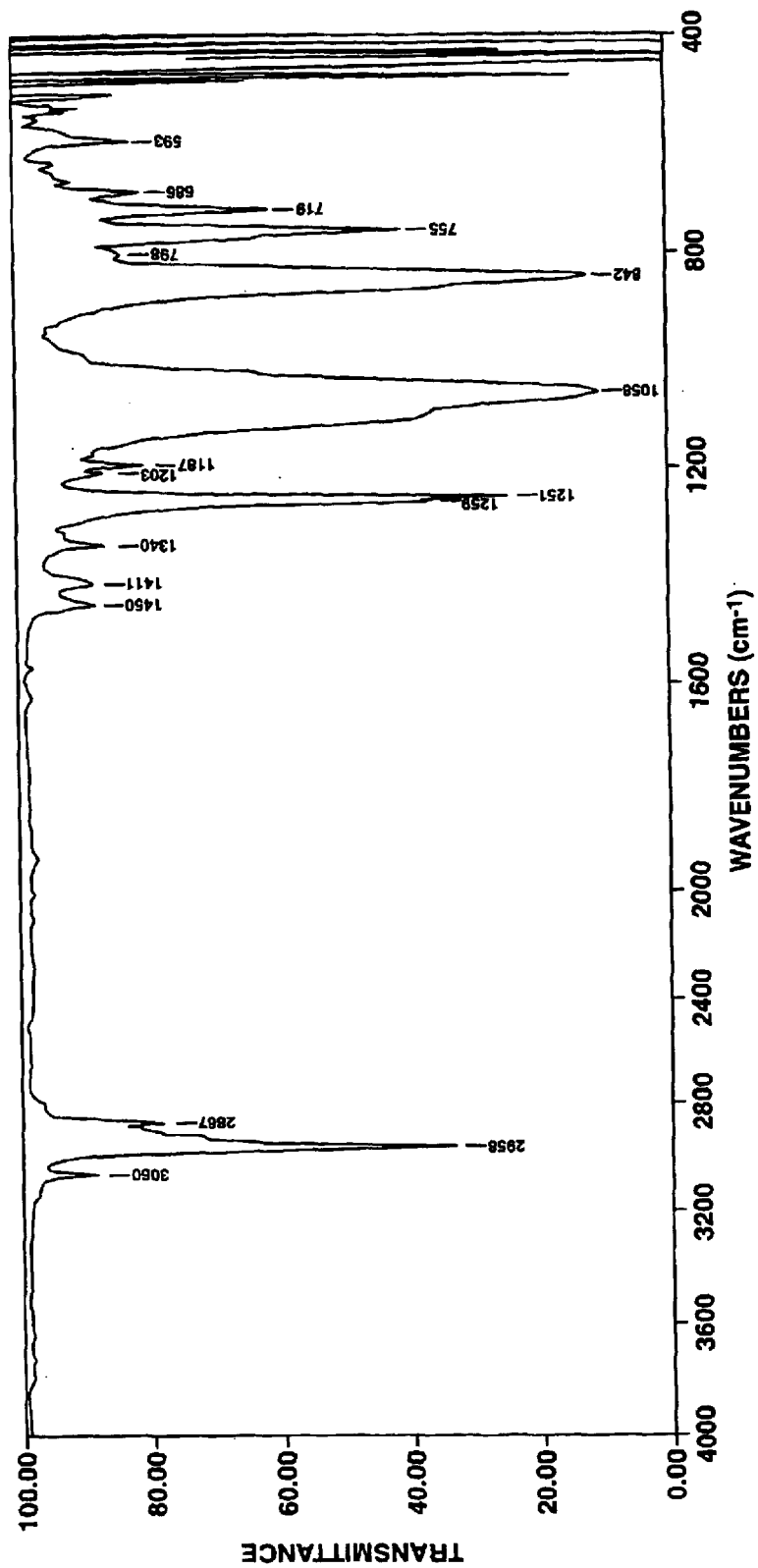

The reaction solution was subjected to separatory operation to remove the aqueous layer. While the organic layer was kept at a temperature of 20–25° C., 23.5 g (0.24 mol) of conc. sulfuric acid was added dropwise over 15 minutes, and stirring was continued at the temperature for 1.75 hours. The organic layer after reaction with sulfuric acid was analyzed by GC, finding that the area percent ratio of the main product to monomethoxy and monohydroxy compounds, NBE-Si(OSiMe$_3$)$_3$/[NBE-Si(OMe)(OSiMe$_3$)$_2$+NBE-Si(OH)(OSiMe$_3$)$_2$] was 278.1. The sulfuric acid layer was removed from the reaction solution, after which the organic layer was washed with water, neutralized with aqueous sodium bicarbonate, and washed with water again. On distillation of the resulting organic layer, 294.8 g (0.707 mol) of a product with a purity of 99.7% was collected as a fraction having a boiling point of 119.0–123.0° C./0.3 kPa. The yield was 88.4%. Proton-NMR and IR spectrum of the fraction were measured. FIG. 1 is a chart of $^1$H-NMR in heavy chloroform solvent and FIG. 2 is the IR spectrum.

From these data, the fraction was identified to be 2-(5-norbornenyl)ethyltris(trimethylsiloxy)silane.

Example 16

A 1000-ml four necked glass flask equipped with a reflux condenser, thermometer and stirrer was purged with nitrogen. The flask was charged with 186.4 g (1.0 mol) of 1,3-divinyl-1,1,3,3-tetramethyldisiloxane and 25.6 g (0.8 mol) of methanol, and cooled in an ice water bath to an internal temperature below 10° C. To the flask kept at an internal temperature of 5–10° C., 3.92 g (0.04 mol) of conc. sulfuric acid was added dropwise over 30 minutes, and stirring was continued at the temperature for 30 minutes.

Subsequently, to the flask kept at an internal temperature of 5–10° C., 97.0 g (0.4 mol) of 2-(5-norbornenyl)ethyltrimethoxysilane was added dropwise over 30 minutes, and stirring was continued at the temperature for one hour. At an internal temperature of 5–25° C., 28.8 g (1.6 mol) of water was added dropwise over one hour. After the completion of dropwise addition, stirring was continued at 50–55° C. for 12 hours. The organic layer of the reaction solution was analyzed by GC, finding that the area percent ratio of the main product to monomethoxy and monohydroxy compounds, NBE-Si(OSiMe$_2$Vi)$_3$/[NBE-Si(OMe)(OSiMe$_2$Vi)$_2$+NBE-Si(OH)(OSiMe$_2$Vi)$_2$] was 16.3. The total content of monomethoxy and monohydroxy compounds was 0.02 mol, as determined from the area percents by GC.

Figure 3:
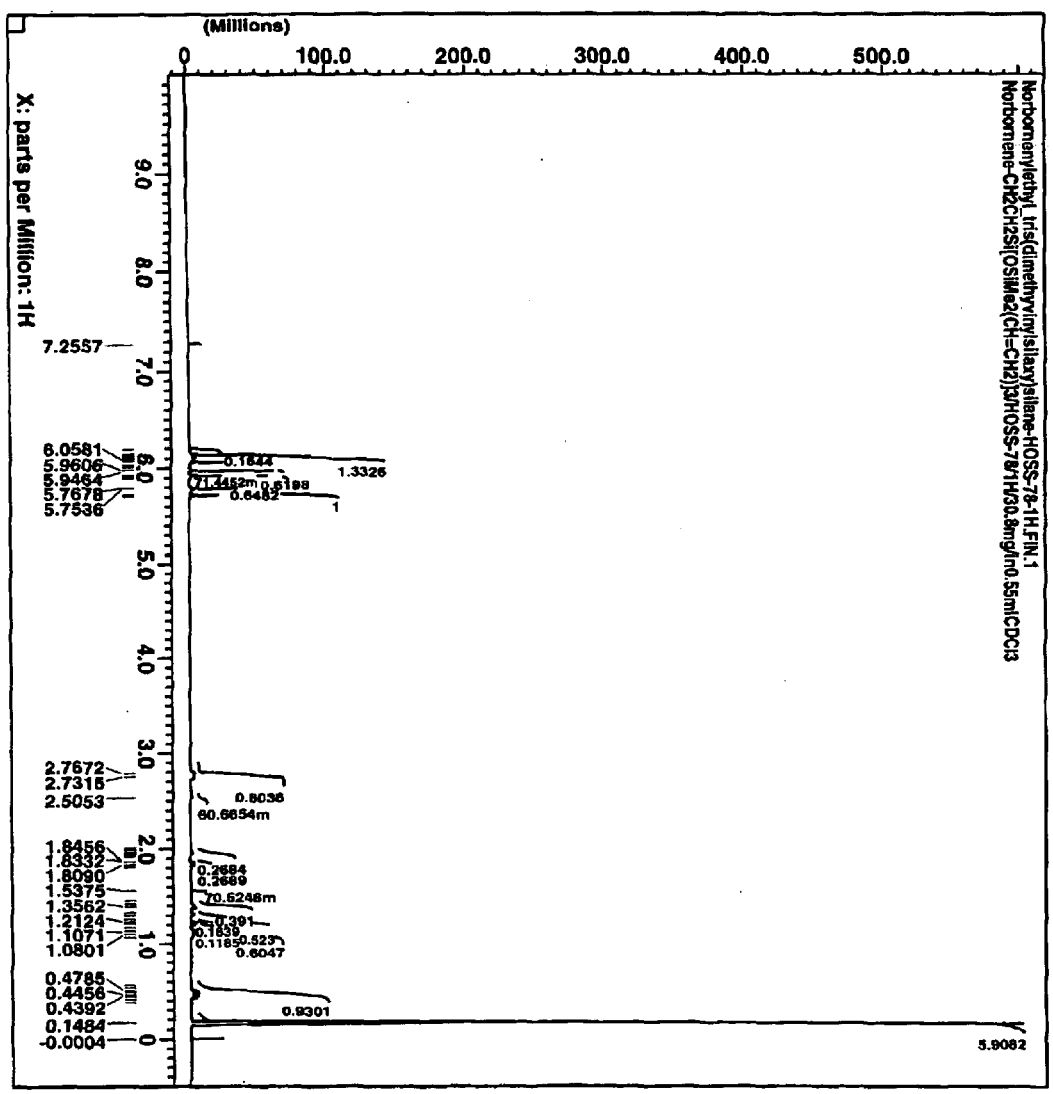
FIGS. 3 and 4 are charts of $^1$H-NMR (in heavy chloroform solvent) and IR spectrum of the product of Example 16, respectively.
Figure 4:
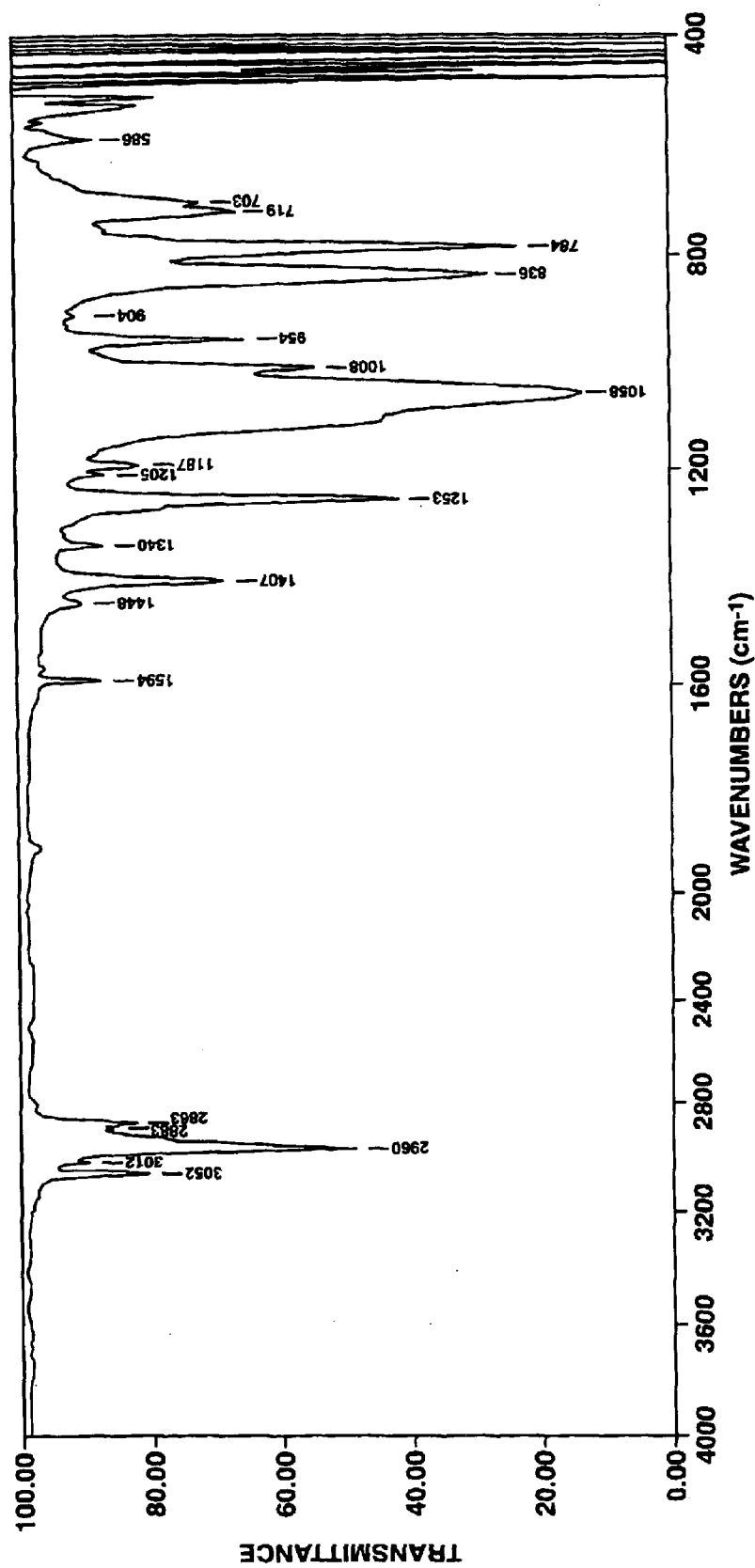

The reaction solution was subjected to separatory operation to remove the aqueous layer. While the organic layer was kept at a temperature of 20–25° C., 11.8 g (0.12 mol) of conc. sulfuric acid was added dropwise over 15 minutes, and stirring was continued at the temperature for one hour. The organic layer after reaction with sulfuric acid was analyzed by GC, finding that the area percent ratio of the main product to monomethoxy and monohydroxy compounds, NBE-Si(OSiMe$_2$Vi)$_3$/[NBE-Si(OMe)(OSiMe$_2$Vi)$_2$+NBE-Si(OH)(OSiMe$_2$Vi)$_2$] was 166.1. The sulfuric acid layer was removed from the reaction solution, after which the organic layer was washed with water, neutralized with aqueous sodium bicarbonate, and washed with water again. On distillation of the resulting organic layer, 131.3 g (0.29 mol) of a product with a purity of 99.2% was collected as a fraction having a boiling point of 132.0–134.0° C./0.1 kPa. The yield was 72.5%. Proton-NMR and IR spectrum of the fraction were measured. FIG. 3 is a chart of $^1$H-NMR in heavy chloroform solvent and FIG. 4 is the IR spectrum.

From these data, the fraction was identified to be 2-(5-norbornenyl)ethyltris(dimethylvinylsiloxy)silane.

Example 17

A 1000-ml four necked glass flask equipped with a reflux condenser, thermometer and stirrer was purged with nitrogen. The flask was charged with 152.2 g (1.0 mol) of tetramethoxysilane and 96.0 g (3.0 mol) of methanol, and cooled in an ice water bath to an internal temperature below 10° C. To the flask was added 2.1 g (0.02 mol) of 35% hydrochloric acid. Subsequently, to the flask kept at an internal temperature of 5–10° C., 470.1 g (3.5 mol) of 1,1,3,3-tetramethyldisiloxane was added dropwise over 2.5 hours, and stirring was continued at the temperature for 1.5 hours. At an internal temperature of 7–21° C., 104.4 g (5.8 mol) of water was added dropwise over one hour. After the completion of dropwise addition, stirring was continued at 15–25° C. for 1.5 hours. The organic layer of the reaction solution was analyzed by GC, finding that the area percent ratio of the main product to monomethoxy compound, Si(OSiMe$_2$H)$_4$/Si(OMe)(OSiMe$_2$H)$_3$ was 33.9. The content of monomethoxy compound was 0.027 mol, as determined from the area percents by GC.

The reaction solution was subjected to separatory operation to remove the aqueous layer. While the organic layer was kept at a temperature of 5–15° C., 17.6 g (0.18 mol) of conc. sulfuric acid was added dropwise over 15 minutes, and stirring was continued at the temperature for two hours. The organic layer after reaction with sulfuric acid was analyzed by GC, finding that the area percent ratio of the main product to monomethoxy compound, Si(OSiMe$_2$H)$_4$/Si(OMe)(OSiMe$_2$H)$_3$ was 404.8. The sulfuric acid layer was removed from the reaction solution, after which the organic layer was washed with water, neutralized with aqueous sodium bicarbonate, and washed with water again. On distillation of the resulting organic layer, 293.4 g (0.89 mol) of tetrakis(dimethylsiloxy)silane with a purity of 99.7% was collected as a fraction having a boiling point of 96.0–96.5° C./4.3 kPa. The yield was 89.3%.

Comparative Example 1

A 1000-ml four necked glass flask equipped with a reflux condenser, thermometer and stirrer was purged with nitrogen. The flask was charged with 136.2 g (1.0 mol) of methyltrimethoxysilane, 324.8 g (2.0 mol) of hexamethyldisiloxane and 64.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 15 minutes, and stirring was continued at the temperature for 30 minutes. Subsequently, at a temperature of 5–25° C., 105.0 g (5.83 mol) of water was added dropwise over one hour. After the completion of dropwise addition, stirring was continued at 15–25° C. for 3 hours. The aqueous layer was removed from the reaction solution, after which the organic layer was washed with aqueous sodium bicarbonate and then with water. On distillation of the resulting organic layer, 225.3 g (0.73 mol) of methyltris(trimethylsiloxy)silane with a purity of 99.5% was collected as a fraction having a boiling point of 120.0–120.5° C./12 kPa. The yield was 72.5%.

Comparative Example 2

A 1000-ml four necked glass flask equipped with a reflux condenser, thermometer and stirrer was purged with nitrogen. The flask was charged with 136.2 g (1.0 mol) of methyltrimethoxysilane, 372.8 g (2.0 mol) of 1,1,3,3-tetramethyl-1,3-divinyldisiloxane and 96.0 g (2.0 mol) of methanol, and cooled in an ice water bath to an internal temperature below 10° C. To the flask kept at an internal temperature of 5–10° C., 9.8 g (0.1 mol) of conc. sulfuric acid was added dropwise over 15 minutes, and stirring was continued at the temperature for 30 minutes. Subsequently, at a temperature of 5–25° C., 105.0 g (5.83 mol) of water was added dropwise over one hour. After the completion of dropwise addition, stirring was continued at 15–25° C. for 2.5 hours. The aqueous layer was removed from the reaction solution, after which the organic layer was washed with aqueous sodium bicarbonate and then with water. On distillation of the resulting organic layer, 217.0 g (0.63 mol) of methyltris(trimethylsiloxy)silane with a purity of 99.7% was collected as a fraction having a boiling point of 102.0–103.0° C./1.3 kPa. The yield was 62.8%.

Japanese Patent Application No. 2003-303849 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for preparing a branched siloxane of the general formula (2), comprising the step of:

reacting a branched siloxane compound of the general formula (2) containing a compound of the general formula (1) as an impurity with a disiloxane compound of the general formula (3) in the presence of an acid compound, for forming a branched siloxane of formula (2) containing a reduced level of the compound of formula (1), $$R^1{}_n Si(OSiR^2{}_3)_{3-n}(OR^3) \quad (1)$$

wherein $R^1$ is a substituted or unsubstituted monovalent hydrocarbon group of 1 to 20 carbon atoms, $R^2$ and $R^3$ are selected from hydrogen and substituted or unsubstituted monovalent hydrocarbon groups of 1 to 20 carbon atoms, $R^2$ may be the same or different, n is equal to 0 or 1, $$R^1{}_n Si(OSiR^2{}_3)_{4-n} \quad (2)$$

wherein $R^1$, $R^2$ and n are as defined above, $$R^2{}_3 SiOSiR^2{}_3 \quad (3)$$

wherein $R^2$ is as defined above.

2. The method of claim 1, wherein the acid compound is used in at least an equimolar amount relative to the total of the compound of formula (1).

3. The method of claim 1, wherein the branched siloxane compound of formula (2) containing the compound of formula (1) as an impurity has been synthesized by reacting a disiloxane compound of formula (3) with an organoxysilane compound of the general formula (4):

$$R^1{}_n Si(OR^4)_{4-n} \quad (4)$$

wherein $R^1$ is as defined above, $R^4$ is a substituted or unsubstituted monovalent hydrocarbon group of 1 to 20 carbon atoms, and n is equal to 0 or 1, in the presence of an acid catalyst.

4. The method of claim 3, wherein the branched siloxane compound of formula (2) containing the compound of formula (1) as an impurity has been synthesized by adding the organoxysilane compound of formula (4) to a liquid mixture of the disiloxane compound of formula (3), an alcohol and the acid catalyst for reaction, and further adding water for effecting co-hydrolysis.

5. The method of claim 1, wherein the branched siloxane compound of formula (2) is selected from the group consisting of methyltris(trimethylsiloxy)silane, tetrakis(trimethylsiloxy)silane, 3-acryloxypropyltris(trimethylsiloxy)silane, 3-methacryloxypropyltris(trimethylsiloxy)silane, p-styryltris(trimethylsiloxy)silane, 5-norbornenyltris(trimethylsiloxy)silane, 2-(5-norbornenyl)ethyltris(trimethylsiloxy)silane, and 2-(5-norbornenyl)ethyltris(dimethylvinylsiloxy)silane.

6. The method of claim 1, wherein the acid compound is sulfuric acid.

* * * * *